(12) United States Patent
Tatum (10) Patent No.: US 6,258,327 B1
(45) Date of Patent: Jul. 10, 2001

(54) BIOPSY SPECIMEN COLLECTION DEVICE

(76) Inventor: E. Terry Tatum, 1617 Euclid Ave., Bowling Green, KY (US) 42103

(*) Notice: Subject to any disclaimer, the term of this patent is extended or adjusted under 35 U.S.C. 154(b) by 0 days.

(21) Appl. No.: 09/248,802

(22) Filed: Feb. 11, 1999

Related U.S. Application Data (60) Provisional application No. 60/080,554, filed on Apr. 3, 1998.

(51) Int. Cl.$^7$ .................................................... C12M 1/40
(52) U.S. Cl. .................. 422/102; 435/287.9; 435/288.4; 435/305.3; 422/104; 425/542
(58) Field of Search .............................. 435/287.9, 284.1, 435/288.4, 305.3, 305.4, 307.1; 600/564; 609/317.903; 378/164, 208; 206/438, 569; 422/101, 102, 109

(56) References Cited

U.S. PATENT DOCUMENTS

| | | |
|---|---|---|
| D. 253,126 | 10/1979 | Baxter . |
| D. 253,127 | 10/1979 | Baxter . |
| D. 258,761 | 3/1981 | Graham . |
| D. 303,149 | 8/1989 | Andersen . |
| D. 324,271 | 2/1992 | Frenkel et al. . |
| D. 338,965 | 8/1993 | Glanz et al. . |
| D. 367,932 | 3/1996 | Lim . |
| 2,935,384 | 5/1960 | Schalm et al. . |
| 2,965,219 | 12/1960 | Rhodin . |
| 3,441,383 | 4/1969 | Moore et al. . |
| 3,938,961 | 2/1976 | Lanier . |
| 4,837,795 | 6/1989 | Garrigus . |
| 5,524,634 | 6/1996 | Turkel et al. . |
| 5,609,827 | 3/1997 | Russell et al. . |
| 5,679,570 | 10/1997 | Heckenmuller et al. . |

Primary Examiner—Lyle A. Alexander
(74) Attorney, Agent, or Firm—Vance A. Smith; David W. Nagle, Jr.; Stites & Harbison

(57) ABSTRACT

The present invention is a biopsy specimen collection device having chambers, for receiving tissue samples of differing sizes from various locations within a particular anatomical organ or system, consolidated on a base or tray. The site-specific chambers of the collection device are mounted over a schematic diagram of the anatomical organ or organ system from which the specimens are being collected, and an identification panel, having a key for each chamber, allows commentary to be added regarding the particular samples. One or more non-site-specific chambers are also provided to allow the physician maximum collection flexibility, without the need for additional, separate containers. The chambers are filled with a tissue preservative to preserve the specimens for laboratory testing or histological examination.

17 Claims, 9 Drawing Sheets

BIOPSY SPECIMEN COLLECTION DEVICE

This application claims the benefit of Provisional No. 60/080,554 filed Apr. 3, 1998.

BACKGROUND

The present invention is a device for collecting, storing, and transporting medical biopsy specimens.

During a surgical procedure, tissue specimens may be collected through biopsy for laboratory analyses. Frequently, multiple tissue specimens are collected at the same time. For example, during an upper gastrointestinal endoscopy, specimens are collected from the esophagus, the stomach, and the duodenum; a lower gastrointestinal endoscopy collects specimens from the rectum, the left and right colon, and the terminal ileum; a gynecological evaluation uses specimens collected from the cervix, the endocervix, and the endometrium; and a prostate evaluation uses specimens collected at several sites in the prostate gland. As the tissue specimens are collected, they are placed in individual and separate preservative-filled containers or chambers.

Because the specimen containers are sent to a central laboratory for analysis, each container must be labeled with patient identifying information, such as patient name, biopsy site, responsible physician, and an analysis requisition sticker. The process of organizing, labeling, and submitting multiple individual and separate biopsy specimens from a given patient is time consuming and tedious for the submitting doctor and nurse, because of the need for surgical personnel to exchange containers between each specimen collected. The receiving laboratory must also deal with numerous specimen containers from any one patient, increasing the risk of mislabeling or losing one or more specimens.

Specimen collection devices have been designed with several containers joined together. For example, U.S. Pat. No. D367,932, issued to Lim, describes a containment device with several containers joined at the lip, and U.S. Pat. No. 2,935,384, issued to Schalm et al, teaches that containers can be united on a base or a tray. The containers in these devices are uniformly sized and separated from each other by relatively equal distances. The overall design of these containment devices are convenient for conducting standardized laboratory tests, but can be burdensome for the physician to use during a surgical procedure because relatively specific information about the biopsy site must be provided for each individual sample. Further, because the containers are of a uniform size, the biopsy specimens collected must either be of relatively uniform size, or multiple collection devices must be used during a procedure.

A few specimen collection devices have multiple containers that vary in size, such as the device taught in U.S. Pat. No. 5,609,827, issued to Russell et al. These devices assume a primary biopsy site, with other specimens being collected from the immediate vicinity of the primary site. The collection device of the Russell et al patent allows the specimens to be labeled to show the relative positioning of the secondary specimens as compared to the primary specimen, but does not specify the location of the primary site within the body.

SUMMARY OF THE INVENTION

The present invention is a biopsy specimen collection device having chambers, for receiving tissue samples of histological differing sizes from various locations within a particular anatomical organ or system, consolidated on a base or tray. The site-specific chambers of the collection device are mounted over a schematic diagram of the anatomical organ or organ system from which the specimens are being collected, and an identification panel, having a key for each chamber, allows commentary to be added regarding the particular samples. One or more non-site-specific chambers are also provided to allow the physician maximum collection flexibility, without the need for additional, separate containers. The chambers are filled with a tissue preservative to preserve the specimens for laboratory testing or histological examination.

All specimens for a particular procedure from a single patient can be collected on a single tray, thereby improving the efficiency of the submitting clinical personnel and reducing the risk of labeling errors. Because the devices are procedure specific, the specimen chambers can vary in size, to more accurately reflect the samples typically collected from a particular site. By having preservative supplied in the chambers, the efficiency and safety of the clinical personnel is increased because the clinicians do not need to use valuable time measuring out preservative, and the clinicians are not exposed to large quantities of preservative.

DESCRIPTION OF THE PREFERRED EMBODIMENT

The inventor has developed a series of specimen collection devices designed to correspond to biopsy sites from within the body. For example, some of the kinds of collection devices that may be made in accordance with the present invention include devices for collecting, storing, and transporting histological specimens taken from the prostate (FIGS. 1–5A), the upper gastrointestinal (GI) tract (FIG. 6), and the lower gastrointestinal (GI) tract (FIG. 7), the cervix and uterus (FIG. 8). For illustrative purposes only, most of the embodiments described hereafter will refer to a prostate specimen collection device 10, shown in FIG. 1. It is to be understood that the arrangements described in these embodiments could also be used in an upper GI tract specimen collection device 610, in a lower GI tract specimen collection device 710, in a uterine specimen collection device 810, and in specimen collection devices for other biopsy sites in humans and in animals.

Figure 1:
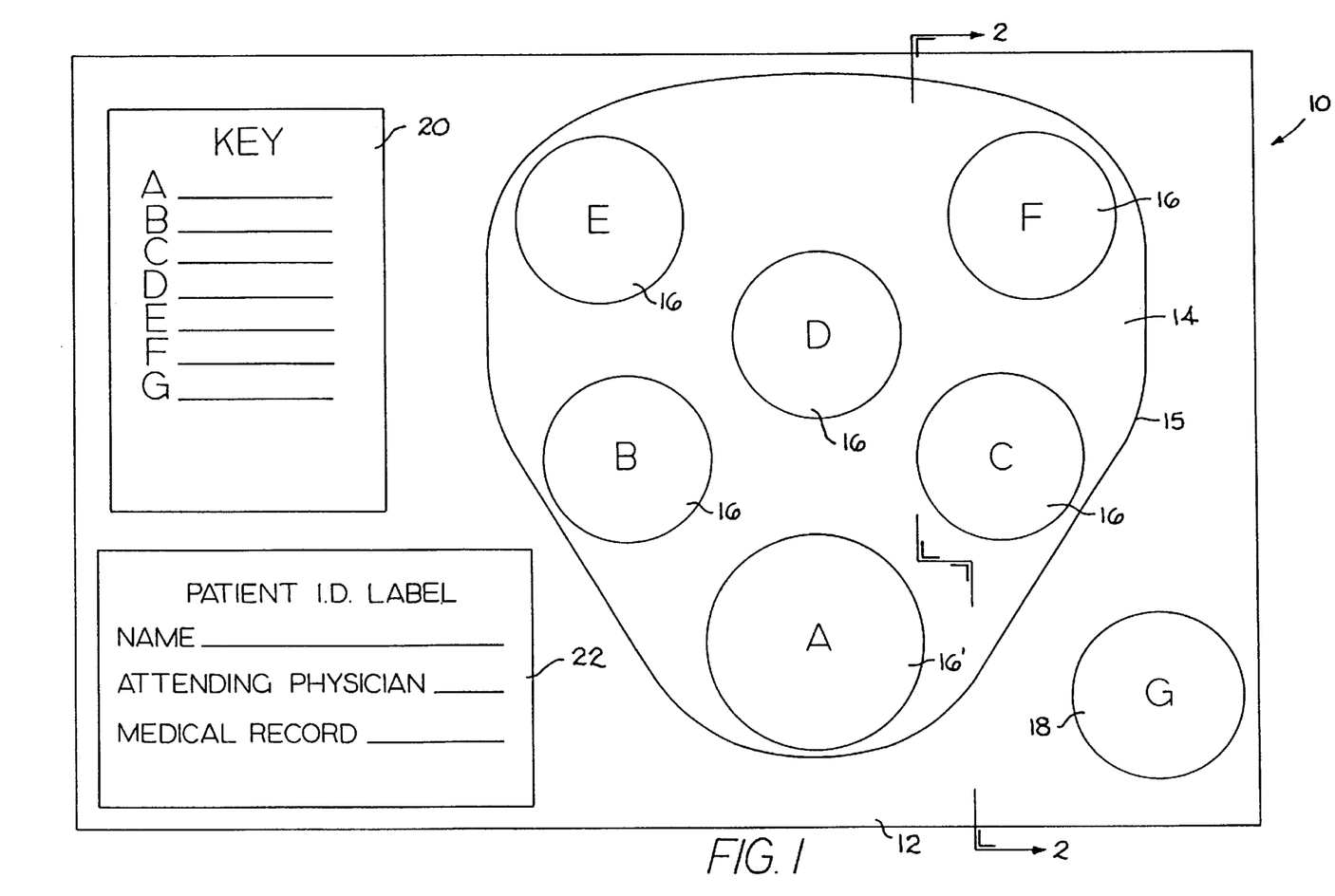
FIG. 1 is a schematic view of a prostate biopsy plate made in accordance with the present invention.
Figure 2A:
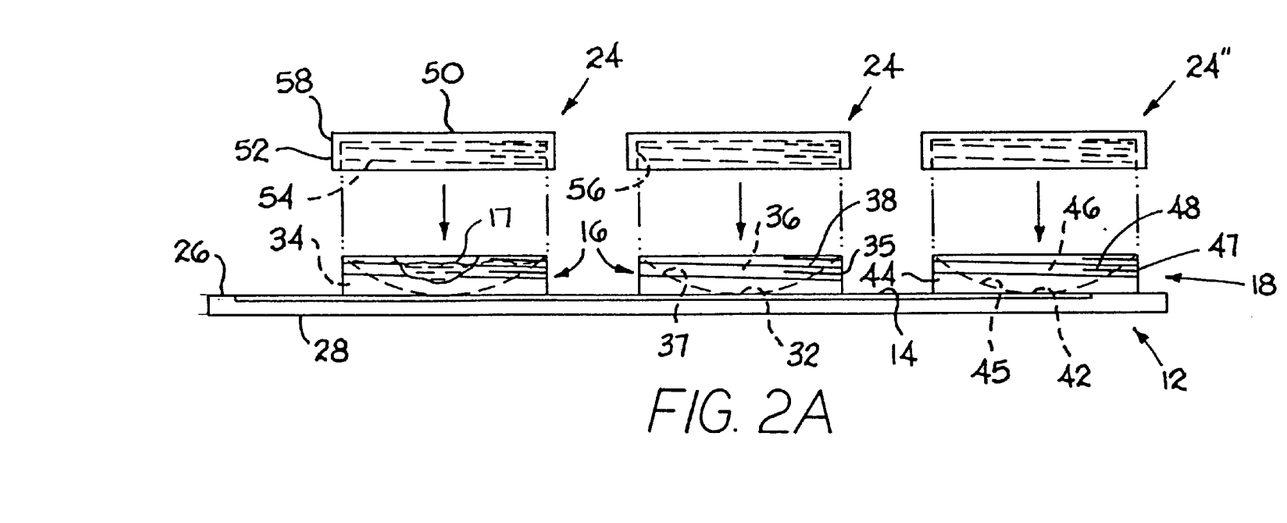
FIG. 2A is a sectional view of the plate illustrated in FIG. 1 along lines 2—2.

Reference is made first to FIG. 1, in which the specimen collection device for receiving specimens from the prostate is generally noted by the character numeral 10. The device of 10 has as major components a base 12, a site map 14, having a periphery 15, specimen chambers 16, 16', 18, and data-entry panels 20, 22. The site map 14 is mounted on the base 12, and the site-specific specimen chambers 16, 16' are mounted over the map 14 within the periphery 15. A non-site-specific chamber 18 is mounted on the base 12, outside the periphery 15 of the map 14. A site identification panel 20 and a patient identification panel 22 are mounted on the base 12 so as not to obstruct the site map 14. The specimen collection device further includes removable caps 24, 24', 24", best seen in FIG. 2, which fit over the chambers 16, 16', 18, respectively, and the chambers 16, 16', 18 can be filled with a predetermined volume of a tissue preservative solution 17.

As seen in FIGS. 1 and 2A, the base 12 is a substantially planar, plate-like element, having a top surface 26 and a bottom surface 28. The size of the base 12 can vary depending on the application, and the number and sizes of the specimen chambers 16, 18 that are to be included on the specimen containment device. The base 12 can be made from any semi-rigid, resilient polymeric material which is chemically inert when exposed to tissue preservatives, such as formalin. Example materials which can be used to make base 12 include polypropylene, polyethylene, polycarbonate, polystyrene, polyurethane, and combinations thereof.

Figure 2B:
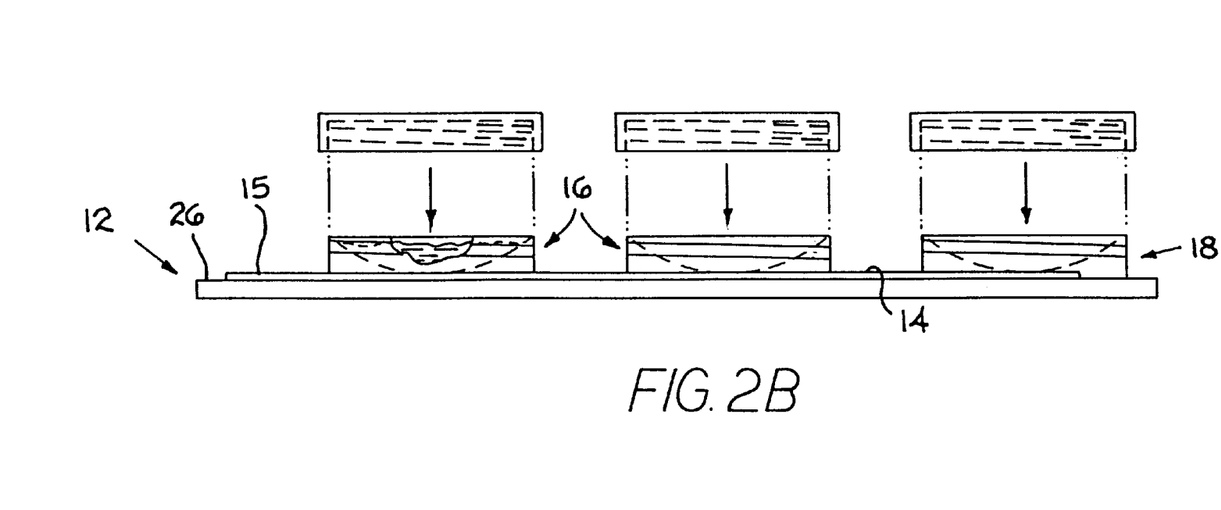
FIG. 2B is a sectional view of an alternative embodiment of the prostate biopsy plate of FIG. 1, taken along a similar line as shown in FIG. 2A.

The site map 14 is a schematic diagram of the anatomical organ or organ system from which the tissue specimens are to be collected. The anatomic organ system depicted can represent a single organ, or multiple organs that are interconnected either physiologically or functionally. The size of the map 14 can vary depending on the application and the number of specimen chambers 16 that are to be included over the map 14. However, the entire periphery 15 should fit on the top 26 of the base 12. The map 14 can be made from any imprintable material, such a paper, paperboard, foil, plastic film, or a combination thereof, and is secured to the base 12 by any acceptable means, such as adhesives or glues. Preferably, the map 14 is made from a material that includes a protective coating layer, such as a plastic film layer, so that the printing on the map 14 is protected from biological specimens and tissue preservatives. Alternatively, the need for an imprintable material and a securing means can be eliminated by having the site map 14 etched into the base 12, as shown in FIG. 2A, or by having the periphery 15B indicated as a protrusion on the top surface 26, as shown in FIG. 2B.

One or more site-specific collection chambers 16 are positioned over the site map 14 to approximate the site or location within the particular anatomical organ or organ system from which the specimen is being taken. The chambers 16 are containers made from glass or any semi-rigid or rigid polymeric material which is chemically inert when exposed to tissue preservatives, such as polypropylene, polyethylene, polycarbonate, polystyrene, polyurethane, and combinations thereof. The chambers 16 have a bottom face 32, a side wall 34, having an interior surface 35 and an exterior surface 37, and a central cavity 36; and can be any shape, such as, round, square, or rectangular. The chambers 16 can be of variable sizes, and are sized to accommodate the anticipated tissue specimen from a particular site plus an appropriate amount of specimen preservative 17. Preferably, the chambers 16 have relatively wide bottoms 32 and relatively short side walls 34, thereby keeping the center of gravity low and stabilizing the specimen collection device during use. The interior surface 35 of the side wall is preferably smooth, so that the tissue specimen can move within the cavity 36 without being torn or otherwise damaged, and the interior surface 35 may be slightly curved, as shown, or essentially perpendicular to the bottom 32. The chambers 16 are secured to the map 14 using any appropriate means, such as adhesives or glue. Alternatively, the chambers 16, base 12, and site map 14 can be formed as a single piece, such as by injection molding, with the chambers 16 being formed over the site map 14.

Because the physician may wish to record more extensive notes related to a particular specimen than merely the site from which the specimen was collected, the individual chambers 16 are preferably differentiated by a code or key, such as a letter or number. The key can be positioned at any location relative to the chambers 16 that will allow the clinical personnel to quickly identify an individual chamber. For example, the key can be printed on the side wall exterior 37; it can be etched into the side wall interior 35 or into the chamber bottom 32; it can be printed on the site map 14 and legible through the chamber bottom 32; or it can be printed on the site map 14 such that it appears to be adjacent to the chamber 16. The individual specimens can be referred to by the key for commentary recorded either on the data-entry panel 20, as will be described later, or on the patient's laboratory requisition or medical chart.

To protect the specimen after it has been collected from the patient and transferred to the chamber 16, a cap 24 is provided. The cap 24, which should fit tightly on the chamber 16 so as to create a relatively waterproof seal, has a top 50 and a side lip 52, having an interior surface 54 and an exterior surface 56. Examples of types of caps 24 which can be used include "pop-on" caps, threaded screw-on caps, and caps which will similarly securely seal the chamber 16. If threaded caps are used, the cap 24 further includes threads 58 on the inside surface 54, and the exterior side walls 37 of the chamber 16 should further include threads 38 to complement the cap threading 58. The cap 24 can be made from glass or any semi-rigid or rigid polymeric material which is chemically inert when exposed to tissue preservatives, such as polypropylene, polyethylene, polycarbonate, polystyrene, polyurethane, and combinations thereof. Preferably, the caps 24 will be clear or translucent so that the chamber 16 contents can be viewed through the top 50. The cap 24 may further include a code or key, such as a letter or number, visible on either the top 50 or the side lip 52.

During a biopsy procedure, the physician may have occasion to obtain specimens other than those collected in the site-specific chambers 16. For example, the number of specimens taken from a particular location within an organ may exceed the number of site-specific chambers provided, or a specimen may be collected from a location which does not have an associated site-specific chamber. To provide the physician with maximum sampling flexibility, one or more "non-site-specific" collection chambers 18, having a structure similar to that of chamber 16, may be positioned outside of the periphery 15 of the site map 14. The chambers 18 can be secured to the base 12 using appropriate means, such as adhesives or glue, or they can be formed as a single piece with the base 12, such as by injection molding. The chamber 18 has a bottom face 42, a side wall 44, having an interior surface 45 and an exterior surface 47, and a central cavity 46, and may further include threads 48 on the side wall exterior 47. A code or key, such as a letter or number, can be associated with the chamber 18, in a similar manner to the code or key associated with the chamber 16. This key can provide a reference point for additional notes the physician may wish to include on the data-entry panel 20 or on the patient's laboratory requisition or medical chart. A cap 24" is provided to protect the specimen.

The data entry panels—a site identification panel 20 and a patient identification panel 22—are mounted on the base 12 outside the periphery of the site map 14. The panels 20, 22 can be made from any imprintable material, such a paper, paperboard, foil, plastic film, or a combination thereof. The material used must be receptive to inks, so that data can be entered by the attending medical personnel. The panels 20, 22 are secured to the base 12 by any acceptable means, such as adhesives or glues. Preferably, the panel 20 is preprinted with a code or key corresponding to the key on the chambers 16, 18, and includes blank lines for additional descriptive comments. The panel 22 is preprinted with spaces for patient identifying information, such as name, physician, hospital identification number, patient's clinical history, and the like. If the material of the base 12 is receptive to ink, the panels 20, 22 can be printed or etched directly into the base 12.

The chambers 16, 18 are filled with a predetermined volume of a tissue preservative solution 17. The preservative 17 can be any solution which will retard tissue deterioration, such as buffered formalin.

EXAMPLE 1

Referring again to FIGS. 1 and 2A, a prostate biopsy plate has a base 12; a site map 14, having a periphery 15, mounted on the base 12; five site-specific chambers 16 and one site-specific chamber 16' mounted over the site map 14 within the periphery 15; five caps 24, fitted to the chambers 16, and one cap 24', fitted to the chamber 16'; one non-site-specific chamber 18, a site identification panel 20, and a patient identification panel 22, mounted on the base 12 outside the site map periphery 15; and one cap 24", fitted to the chamber 18. The chambers 16, 16', 18 are filled with 10% buffered formalin.

The base 12 is made from ¼" thick sheet polyethylene, and has a rectangular shape, with sides measuring approximately 4.0" by approximately 6.0". The site map 14 is a schematic diagram of the prostate, including the letters "A", "B", "C", "D", "E", "F", imprinted on 16 mil paperboard and protected with a 8 mil polyethylene film laminated to the imprinted side of the paperboard. The site map 14 is secured to the base 12 with adhesive.

The chambers 16, 16', 18, are made from polyethylene. Each chamber 16 has an essentially flat bottom 32 and an essentially circular side wall 34, the side wall exterior surface 37 diameter being about 2.0 cm, with a height of approximately 1.0 cm, and an interior surface 35 having a concave curvature. The chamber 16' is essentially identical to the chambers 16, except that the side wall exterior surface 37 diameter is about 3.0 cm. The side walls of the chambers 16, 16' include threads 38, 38'. The chambers 16 are positioned over the letters "B", "C", "D" "E" and "F", and the chamber 16' is positioned over the letter "A", such that the letters are legible through the bottoms 32, 32' of the chambers 16, 16'. The chambers 16, 16' are secured to the site map 14 with adhesive. The chamber 18, having threads 48, is essentially identical to the chambers 16 except that the letter "G" is etched into the bottom face 42, and the chamber 18 is secured to the base 12 with adhesive.

The caps 24, 24', 24", are made from polyethylene. Each cap 24, 24" has an essentially flat top 50, an essentially circular side wall 52, having a diameter of slightly greater than about 2.0 cm and height of approximately 0.4 cm, and threads 58 on the inside surface 56 that complement the threads 38, 48. The cap 24' is essentially identical to the cap 24, except the side wall 52' diameter measures slightly greater than about 3.0 cm.

The site identification label 20 has a letter key to correspond to each chamber 16, 16', 18, including blank lines adjacent to each letter, imprinted on 16 mil paperboard and secured to the base 12 with adhesive. The patient identification label 22 is imprinted on 16 mil paperboard and includes blank lines for the patient's name, physician, and medical record number, and is secured to the base 12 with adhesive.

The prostate biopsy plate is assembled by initially securing the site map 14 to the base 12. The chambers 16, 16' are then positioned over the location on the site map 14 that corresponds to the location from which the specimen is to be collected, and the chambers 16, 16' are secured to the map 14. The chamber 18, the site identification label 20, and the patient identification label 22 are secured directly to the base 12. The chambers 16, 18 are filled with approximately 3 cc 10% buffered formalin, and covered with caps 24, 24". The chamber 16' is filled with approximately 5 cc 10% buffered formalin, and covered with cap 24'.

Figure 3:
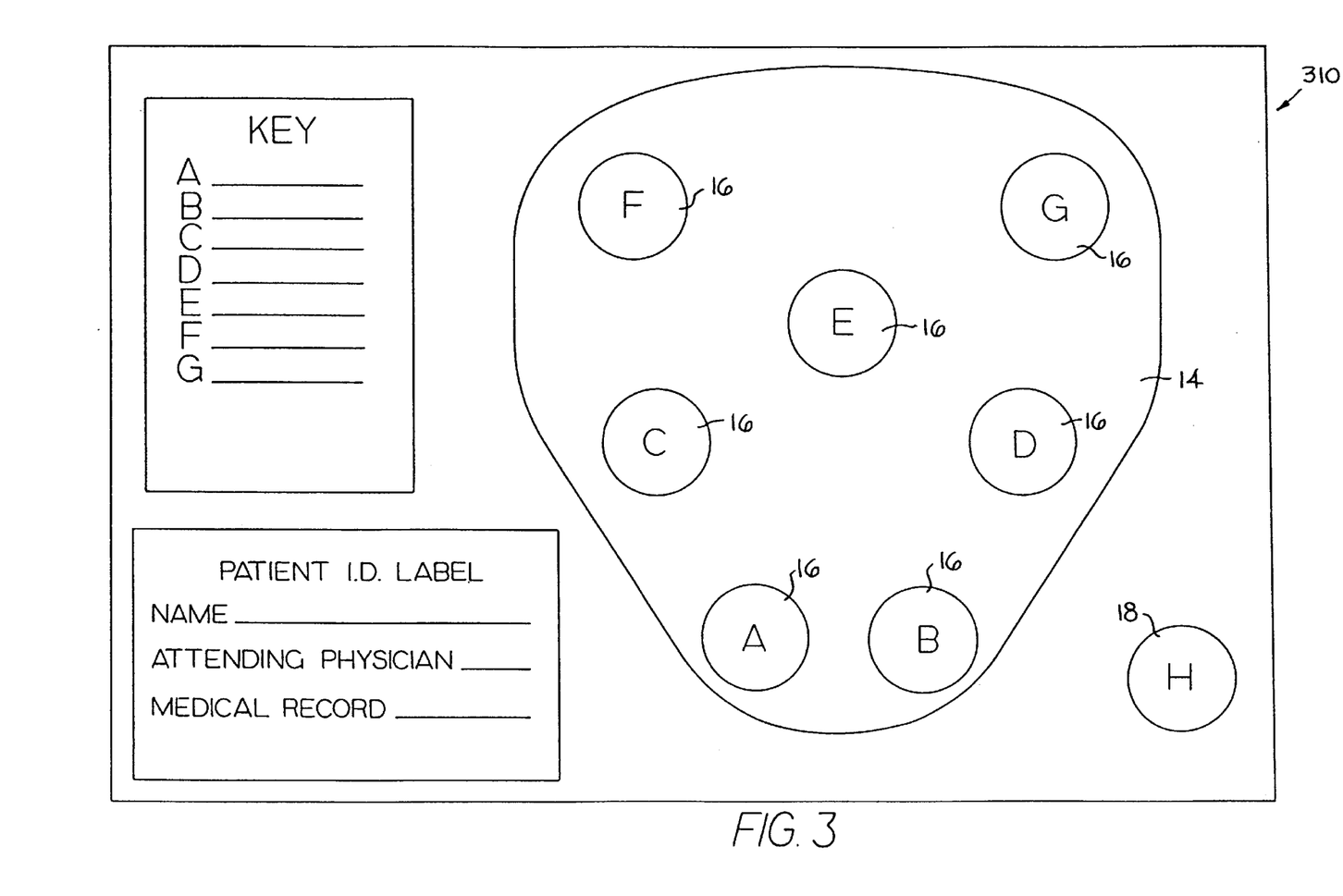
FIG. 3 is schematic view of a second alternative embodiment of the prostate biopsy plate of FIG. 1.

FIG. 3 shows an alternative embodiment of the prostate plate 310. The plate 310 is essentially identical to plate 10 except that the number of the site-specific chambers 16 has been altered to allow for more precise juxtaposing of the site-specific chambers 16 and site map 14 locations corresponding to the actual anatomical locations from which the specimens are to be collected. In accordance with the change in the number of chambers 16, the coding of chambers 16, 18 and the site identification panel 20 key has been altered to reflect the additional chambers 16. Any number of chambers 16, 18 can be used.

Figure 4:
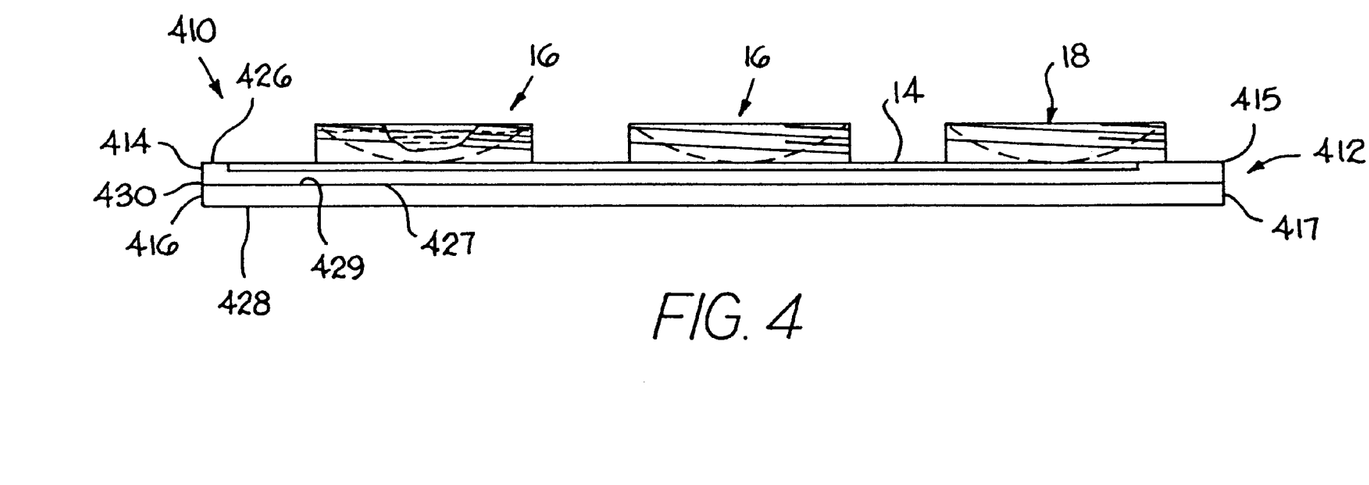
FIG. 4 is a sectional view of a third alternative embodiment of the prostate biopsy plate of FIG. 1, taken along a similar line as shown in FIG. 2A.

In a second alternative embodiment of the prostate biopsy plate 410, the base 12 is replaced by a two-piece base 412, as shown in the sectional view of FIG. 4. The top view of the plate 410 is essentially identical to plate 10 of FIG. 1, and the cross-sectional view of the plate 410 is taken along a line similar to line 2—2. The two-piece base 412 is essentially the same as the base 12, but is made from a first sheet 414 of polymeric material, having a periphery 415, a first top surface 426 and a first bottom surface 427, and a second sheet 416 of polymeric material, having a periphery 417, a second top surface 429 and a second bottom surface 428. The sheets 414, 416, which can be of essentially the same thickness, or of substantially different thicknesses, are positioned such that the first bottom surface 427 creates an interface 430 with the second top surface 429, and the peripheries 415, 417 essentially coincide. The sheets 414, 416 can be secured by any acceptable means, such as adhesives, glue, stainless steel rivets, Teflon-coated brads, and combinations thereof. As shown in FIG. 4, the site map 14 can be mounted on the top surface 426 of the base 412, or alternatively, as shown in FIG. 4A, the site map 14 can be mounted at the interface 430 of the plates 414, 416.

EXAMPLE 2

Figure 4A:
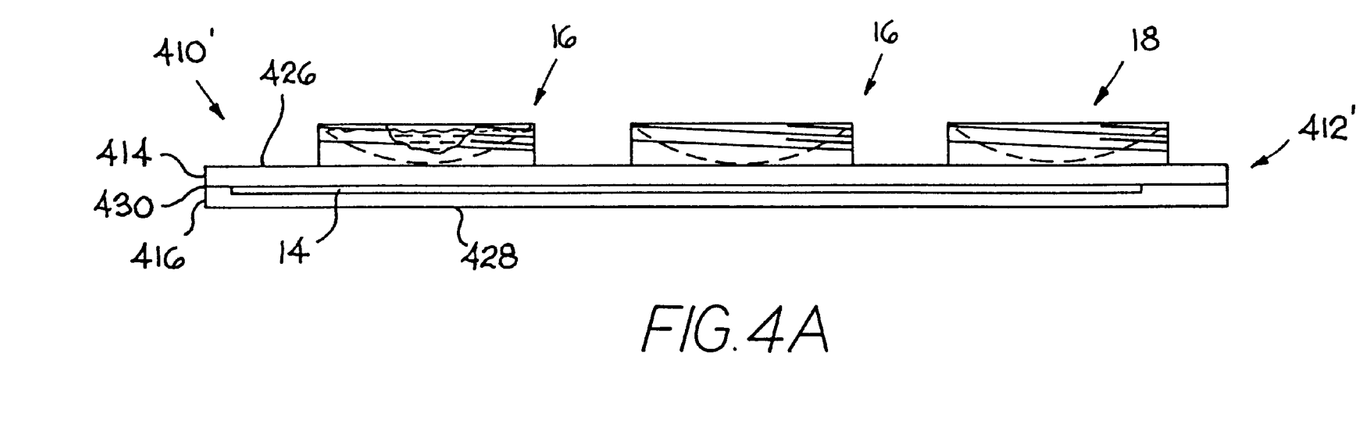
FIG. 4A is a sectional view of a fourth alternative embodiment of the prostate biopsy plate of FIG. 1, taken along a similar line as shown in FIG. 2.

Referring to FIG. 4A, in a preferred embodiment of the prostate biopsy plate 410', a site map 14, chambers 16, 16', 18, caps 24, 24', 24", site identification panel 20, and patient identification panel 22 are the same as in Example 1. A two-piece base 412' is made from a first sheet 414 of polypropylene, having a rectangular shape, with sides measuring approximately 4.0" by approximately 6.0", and a thickness of approximately ⅛", secured to a second sheet 416 of polypropylene, having a rectangular shape, with sides measuring approximately 4.0" by approximately 6.0", and a thickness of approximately ¼". The sheets 414, 416 are secured together with an epoxy adhesive. The site map 14 is positioned at the interface 430, and is held in position by the epoxy adhesive. The chambers 16, 16', 18, and panels 20, 22 are mounted on the first top surface 426 with epoxy adhesive.

Figure 5:
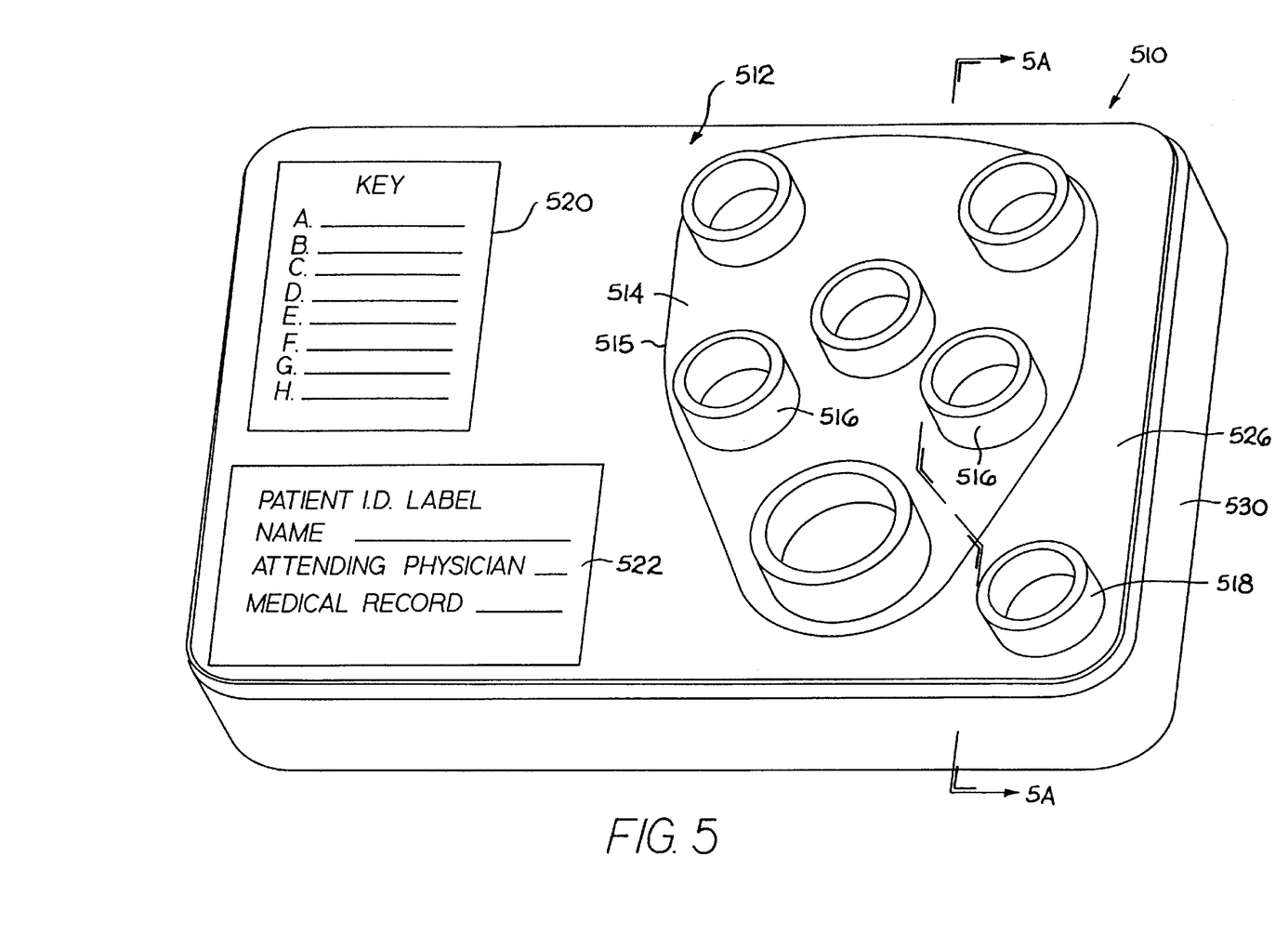
FIG. 5 is a schematic view of a fifth alternative embodiment of the prostate biopsy plate of FIG. 1.
Figure 5A:
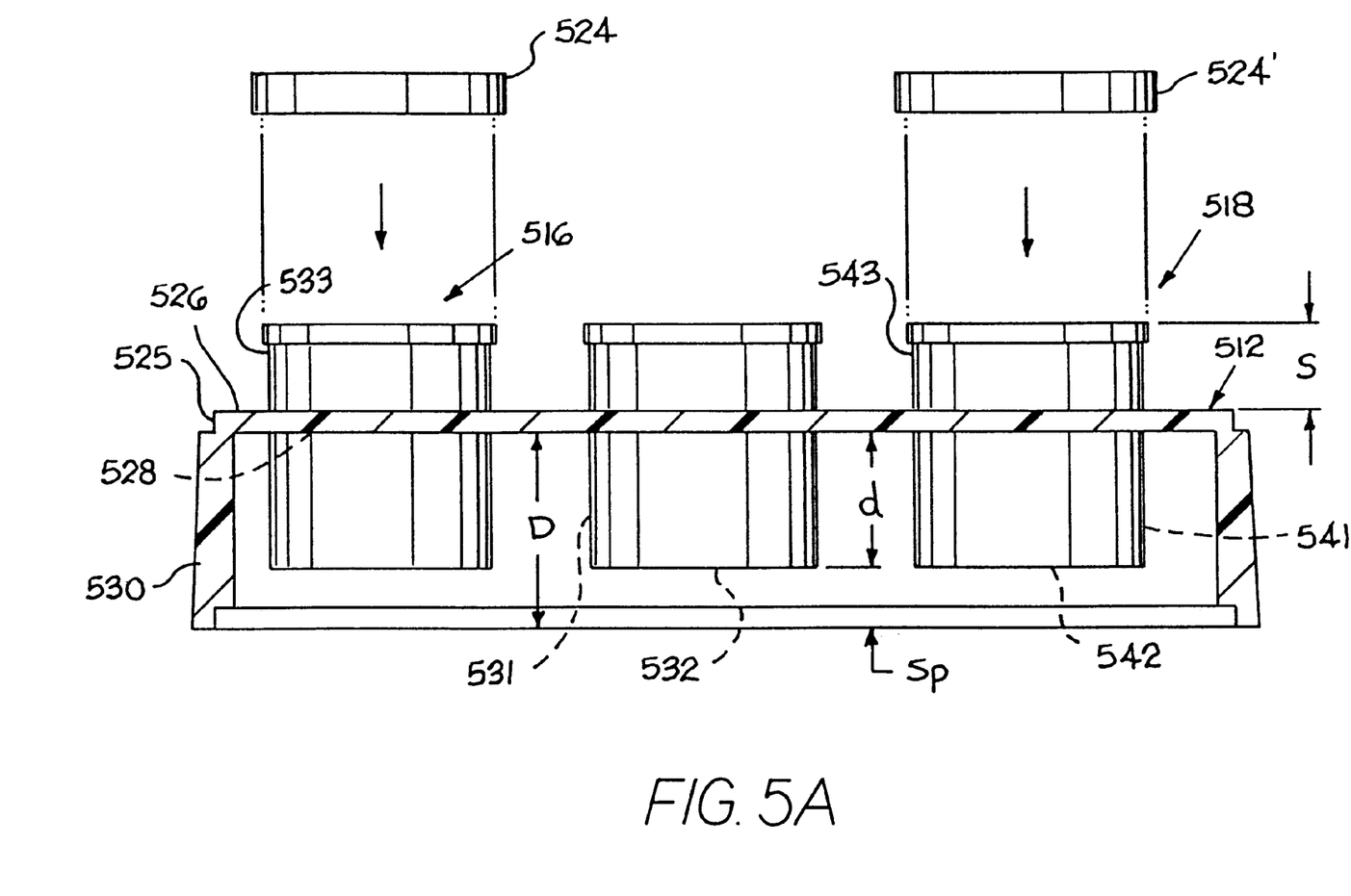
FIG. 5A is a sectional view of the plate illustrated in FIG. 5 along lines 5A—5A.

FIGS. 5 and 5A show a third alternative embodiment of the prostate biopsy plate 510. In this embodiment, the base 512 is a plastic tray having a planar surface 525, including a top face 526 and a bottom face 528, and side walls 530. The side walls 530 extend downward from the bottom face 528 by a predetermined distance "D". The base 512 can be made of any semi-rigid, resilient polymeric material which can be injection molded or stamped into the desired configuration, such as polyethylene, polypropylene, polycarbonate, polystyrene, polyurethane, or combinations thereof. The site map 514 can be essentially the same as site map 14 of FIG. 1, but preferably the map 514 has a periphery 515 that is indicated as a protrusion on the top face 526.

The specimen chambers 516, 518 are made of polymeric materials that are compatible with the base 512 material, and the chambers 516, 518 are preferably injection molded with the base 512 as a single unit. The chambers 516, 518 are mounted on the base 512 such that a first portion of each chamber 531, 541 extends downward from the bottom face 528 by a predetermined distance "d", and a second portion of each chamber 533, 543 projects above the top face 526 by a predetermined distance "s". The distances "d" and "s" should be selected so that the sum "d" plus "s" is less than or equal to the distance "D". This allows one plate 510 to be stacked directly on a second plate 510, which conserves space when storing and transporting the plates. The caps 524, 524', keys, data entry panels 520, 522, and the tissue preservative are essentially identical to the caps 24, 24', keys, data entry panels 20, 22 and preservative 17, described for the prostate biopsy plate 10 of FIG. 1.

Figure 6:
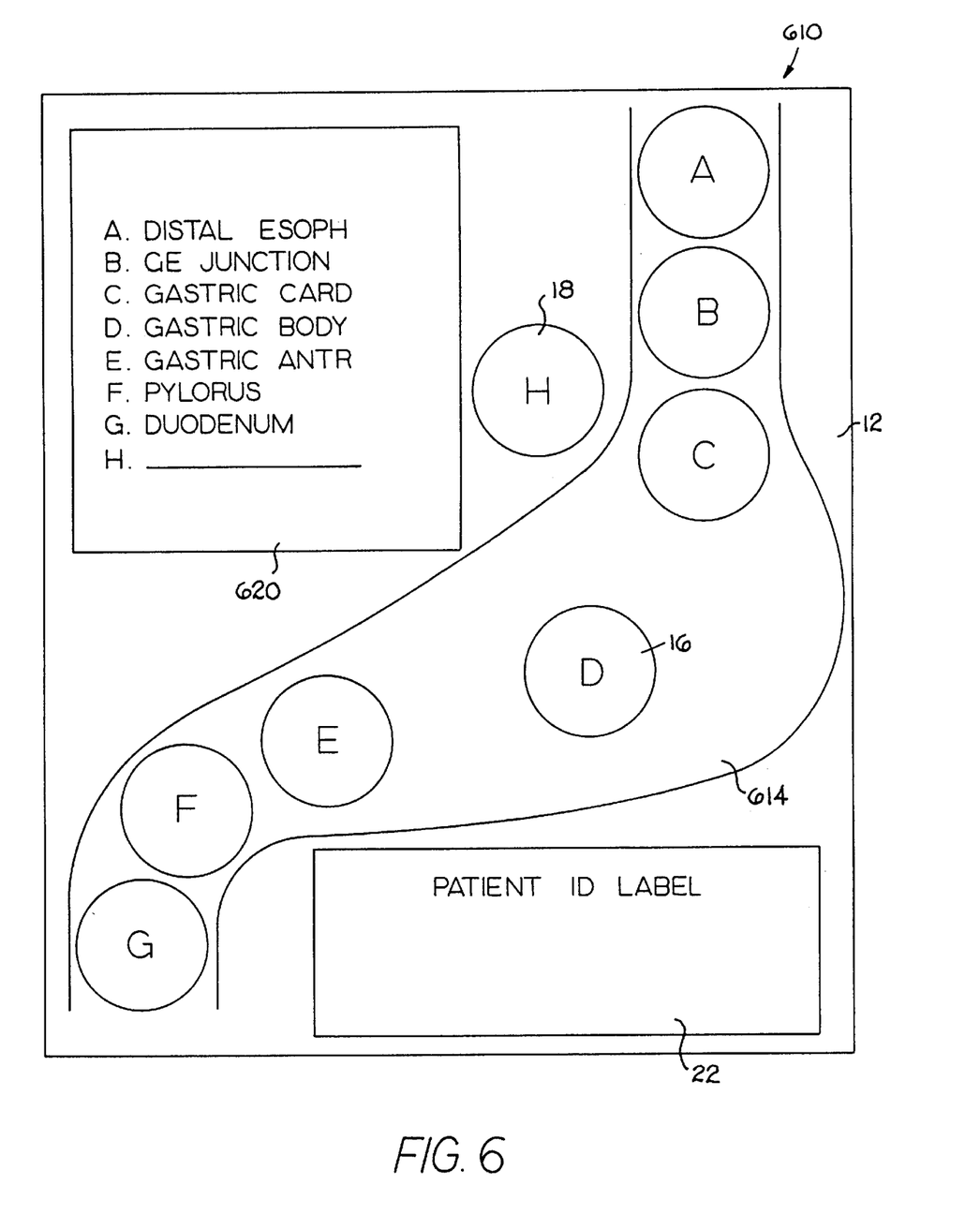
FIG. 6 is a schematic view of an upper gastrointestinal tract biopsy plate made in accordance with the present invention; and, FIG. 7 is a schematic view of a lower gastrointestinal tract biopsy plate made in accordance with the present invention.
Figure 7:
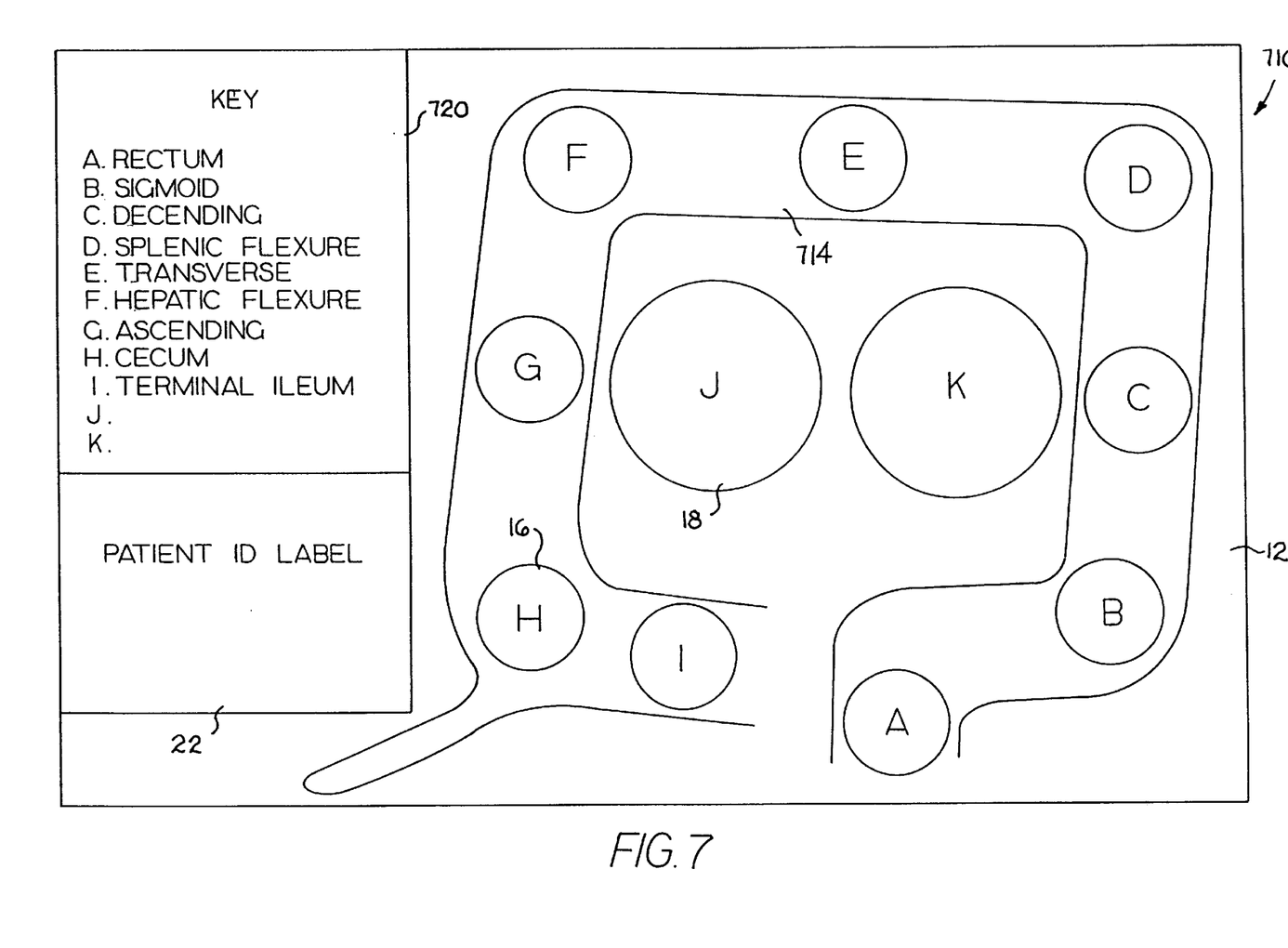
Figure 8:
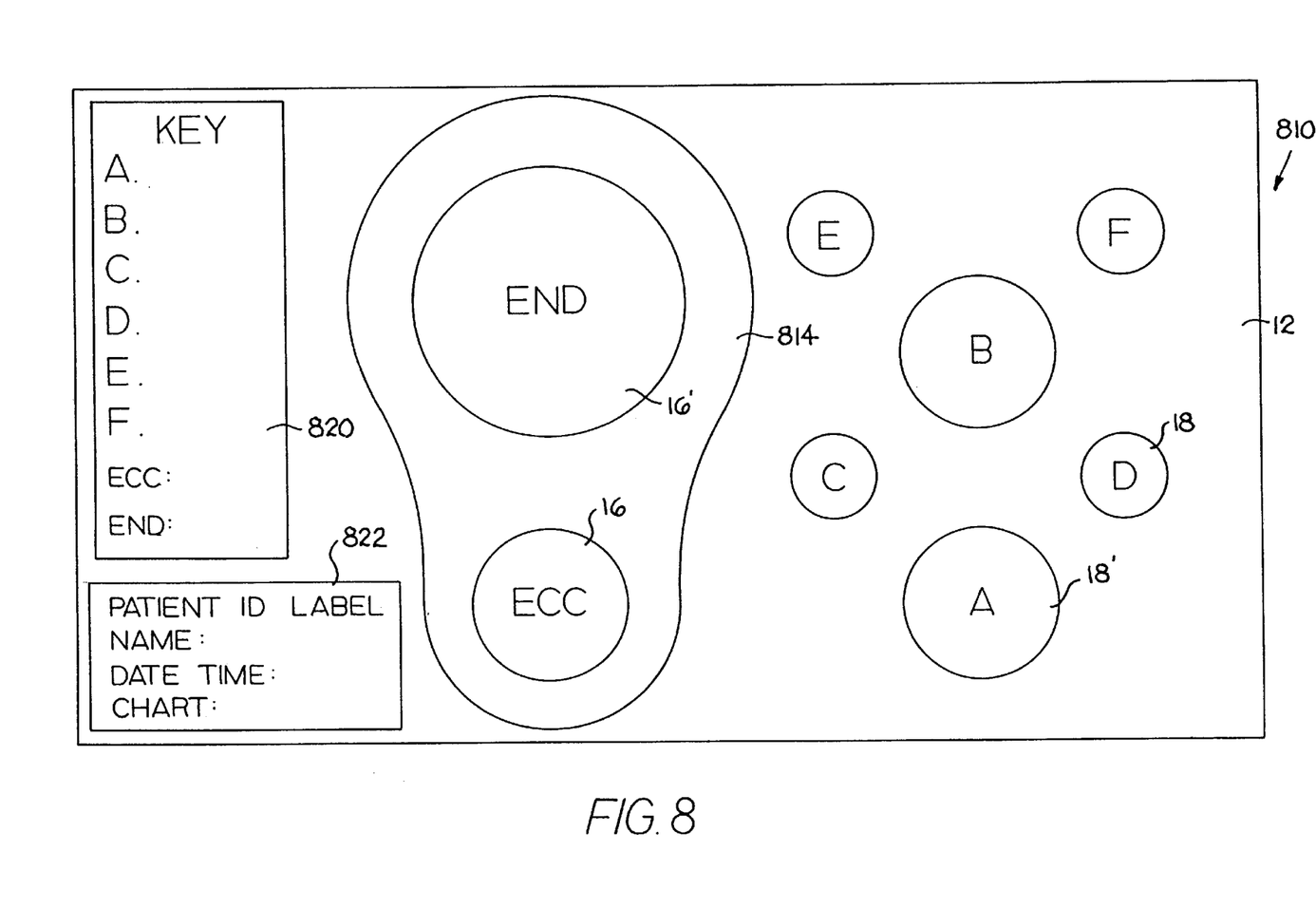
FIG. 8 is a schematic view of a gynecological biopsy plate made in accordance with the present invention.

FIGS. 6, 7, and 8 show an upper gastrointestinal tract biopsy plate 610, a lower gastrointestinal tract biopsy plate 710, and a gynecological biopsy plate 810, respectively. These are examples of some of the kinds of plates that may be made in accordance with the present invention. For each plate 610, 710, 810, the base 12, specimen chambers 16, 16', 18, 18', caps 24, 24', and patient identification panels 22, are made of the same materials as described previously for FIG. 1.

The site maps 614, 714, 814 are made of the same materials as site map 14, described previously for FIG. 1, with different anatomical organs or systems depicted on each plate 610, 710, 810. Because the maps 614, 714, 814 are indicative of the specimen origin, the need for labeling by the surgical personnel is reduced, and the risk of mislabeling the samples is reduced. Further, as best seen by comparing FIG. 1 to FIG. 8, the number and sizes of the site-specific chambers 16, 16', and non-site-specific chambers 18, 18', can vary greatly depending on the particular system for which the biopsy specimen collection device is designed.

The site identification panels 620, 720, 820 are similar to the site identification panel 20, previously described for FIG. 1. However, as illustrated in the key panels 620, 720, 820 information can be preprinted on the panels regarding the specimen collection location. Using partially preprinted site identification panels can improve the efficiency of the surgical personnel while providing flexibility to the physician to include descriptive comments with the specimens.

It will be obvious to those skilled in the art that modifications may be made to the embodiments described above without departing from the scope of the present invention.

What is claimed is:

1. A biopsy specimen collection device for the collection of specimens for histological examination, comprising:
   a base;
   a site map, having a peripheral shape associated with an anatomical organ system, said site map being secured to said base;
   at least one site-specific collection chamber, adapted to receive a biopsy specimen from the organ system, juxtaposed to said site map at a location corresponding to the actual anatomical location from which the specimen is collected from the organ system;
   at least one non-site-specific collection chamber, adapted to receive a biopsy specimen from the organ system, positioned outside the periphery of said site map and secured to the top surface of said base; and
   at least one data entry panel, secured to said base and adapted to have visible indicia imprinted thereon.

2. A specimen collection device as recited in claim 1, wherein said base is a first sheet of polymeric material, having an essentially planar top surface and a periphery.

3. A specimen collection device as recited in claim 1, further including at least one cap removably secured to said site-specific collection chamber, and at least one cap removably secured to said non-site-specific chamber.

4. A specimen collection device as recited in claim 1, wherein said site map is secured to the top surface of said base, and said site-specific collection chambers are secured to said site map.

5. A specimen collection device as recited in claim 2, wherein said site map is secured to a bottom surface of said base, and the site-specific collection chambers are secured to the top surface of said first sheet.

6. A specimen collection device as recited in claim 1, wherein said base is a pair of sheets of polymeric material and said site map is positioned between the sheets.

7. A specimen collection device as recited in claim 1, wherein said site map is etched into said base.

8. A specimen collection device as recited in claim 1, wherein the periphery of said site map protrudes from said base.

9. A specimen collection device as recited in claim 3, further including a predetermined volume of a tissue preservative solution contained within each of said chambers.

10. A specimen collection device as recited in claim 9, wherein the tissue preservative solution is 10% buffered formalin.

11. A specimen collection device as recited in claim 1, wherein said base is a first sheet of polymeric material, having a planar surface and a periphery, and including side walls of a predetermined height that extend downward from the surface along the periphery.

12. A specimen collection device as recited in claim 11, wherein the exterior wall of said site-specific collection chamber and the exterior wall of said non-site-specific collection chamber have a height not greater than the side wall height, so that a plurality of specimen collection devices can be stacked on top of each other.

13. A specimen collection device as recited in claim 12, wherein said site-specific collection chamber protrudes through said base such that a first portion of said chamber is below the planar surface and a second portion of said chamber is above the planar surface, and said non-site-specific collection chamber protrudes through said base such that a first portion of said chamber is below the planar surface and a second portion of said chamber is above the planar surface.

14. A method for making a specimen collection device for the collection of specimens for histological examination, comprising the steps of:

provideing a base;

securing a site map, having a peripheral shape associated with an anatomical organ system, to said base;

securing at least one site-specific specimen chamber, adapted to receive a biopsy specimen from the organ system, to said site map at a location associated with the actual anatomical location from which the specimen is to be collected;

securing at least one non-site-specific specimen chamber, adapted to receive a biopsy specimen from the organ system, to said base at a position outside the periphery of said site map; and securing at least one data entry panel, adapted to have visible indicia imprinted thereon, to said base.

15. A method for making a specimen collection device as recited in claim 14, wherein said base is comprised of a first polymeric material sheet, said site map being secured to a bottom surface of said first sheet, and said site-specific collection chamber, said non-site specific collection chamber, and said data entry panel being secured to a top surface of said first sheet.

16. A method for making a specimen collection device as recited in claim 15, wherein said base includes a second sheet of polymeric material and said site map is positioned between said first and second sheets of material.

17. A method for making a specimen collection device for the collection of specimens for histological examination, comprising the steps of:

injection molding a biopsy plate, the plate including
a planar surface,
side walls, having a predetermined height, projecting downward from a bottom face of the planar surface,
a site map periphery projecting upward from a top face of the planar surface,
at least one site specific collection chamber, having a first portion of predetermined height and a second portion of predetermined height, the first portion projecting upward from the top face of the planar surface at a location within the periphery of the site map that corresponds to the actual anatomical location from which the specimen is collected from an anatomical organ system, and the second portion projecting downward from said bottom surface directly under the first portion, and
at least one non-site specific collection chamber positioned outside the periphery of said site map, having a first portion of predetermined height and a second portion of predetermined height, the first portion projecting upward from the top face of the planar surface, and the second portion projecting downward from said bottom surface directly under the first portion; and securing at least one data entry panel, adapted to have visible indicia imprinted thereon, to said biopsy plate.

* * * * *